US010126547B2

United States Patent
Fujiwara et al.

(10) Patent No.: US 10,126,547 B2
(45) Date of Patent: Nov. 13, 2018

(54) OPTICAL SCANNING APPARATUS

(71) Applicant: OLYMPUS CORPORATION, Tokyo (JP)

(72) Inventors: Masato Fujiwara, Tokyo (JP); Atsuyoshi Shimamoto, Tokyo (JP); Takeharu Innami, Tokyo (JP); Junichi Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 328 days.

(21) Appl. No.: 15/065,969

(22) Filed: Mar. 10, 2016

(65) Prior Publication Data
US 2016/0187647 A1 Jun. 30, 2016

Related U.S. Application Data

(63) Continuation of application No. PCT/JP2014/004646, filed on Sep. 10, 2014.

(30) Foreign Application Priority Data

Sep. 11, 2013 (JP) ................. 2013-188436

(51) Int. Cl.
G02B 26/10 (2006.01)
A61B 1/00 (2006.01)
(Continued)

(52) U.S. Cl.
CPC ........ *G02B 26/103* (2013.01); *A61B 1/00172* (2013.01); *A61B 1/07* (2013.01);
(Continued)

(58) Field of Classification Search
CPC .... G02B 26/103; G02B 26/101; G02B 26/10; G02B 23/2469; G02B 23/2423; A61B 1/00172; A61B 1/07
(Continued)

(56) References Cited

U.S. PATENT DOCUMENTS 6,294,775 B1 * 9/2001 Seibel ................. A61B 1/0008
250/208.1
7,123,790 B2 * 10/2006 Rosman ................ B82Y 35/00
385/25
(Continued)

FOREIGN PATENT DOCUMENTS

JP     2008-116922 A    5/2008
JP     2012-231910 A    11/2012
WO   WO 2013/031824 A1   3/2013

OTHER PUBLICATIONS

International Search Report dated Nov. 25, 2014 issued in PCT/JP2014/004646.

*Primary Examiner* — William R Alexander
(74) *Attorney, Agent, or Firm* — Scully, Scott, Murphy & Presser, P.C.

(57) ABSTRACT

An optical fiber is vibrated at an emitting end part by a scanning part, and light is irradiated from an emitting end face of the optical fiber onto an object to scan the object. The scanning part includes a pair of first direction coils facing each other in a first direction across the emitting end part, and a permanent magnet installed as penetrating the emitting end part. The permanent magnet is magnetized in the axial direction of the emitting end part. The scanning part drives, by supplying power to the first direction coils, the emitting end part to vibrate in the first direction in the second or higher-order resonance mode, forming nodes of the vibration within the permanent magnet. When in a state of non-vibration in the first direction, a relative distance between the permanent magnet and the first direction coils is smaller than that in other directions.

12 Claims, 10 Drawing Sheets

(51) Int. Cl.
*A61B 1/07* (2006.01)
*G02B 23/24* (2006.01)

(52) U.S. Cl.
CPC ......... *G02B 23/2469* (2013.01); *G02B 26/10* (2013.01); *G02B 26/101* (2013.01); *G02B 23/2423* (2013.01)

(58) Field of Classification Search
USPC ...................................................... 359/199.3
See application file for complete search history.

(56) References Cited

U.S. PATENT DOCUMENTS

| | | | | |
|---|---|---|---|---|
| 7,129,472 | B1* | 10/2006 | Okawa | A61B 1/00059 250/234 |
| 7,616,986 | B2* | 11/2009 | Seibel | A61B 5/0062 250/227.26 |
| 7,920,312 | B2* | 4/2011 | Rosman | A61B 5/0062 359/199.1 |
| 8,324,562 | B2* | 12/2012 | Bierhoff | A61B 5/0062 250/227.26 |
| 9,036,232 | B2* | 5/2015 | Birk | G02B 21/002 359/200.7 |
| 10,022,187 | B2* | 7/2018 | Parto | A61B 18/22 |
| 2004/0254474 | A1* | 12/2004 | Seibel | A61B 5/0062 600/473 |
| 2009/0015894 | A1* | 1/2009 | Rosman | A61B 5/0062 359/199.1 |
| 2012/0113491 | A1* | 5/2012 | Hezemans | G02B 21/0012 359/198.1 |
| 2014/0236022 | A1* | 8/2014 | Zeng | A61B 1/00172 600/476 |

* cited by examiner

OPTICAL SCANNING APPARATUS

CROSS REFERENCE TO RELATED APPLICATIONS

The present application is a Continuing Application based on International Application PCT/JP2014/004646 filed on Sep. 10, 2014, which, in turn, claims the priority from Japanese Patent Application No. 2013-188436 filed on Sep. 11, 2013, the entire disclosure of these earlier applications being herein incorporated by reference.

TECHNICAL FIELD

The present disclosure relates to an optical scanning apparatus that uses an oscillatable optical fiber.

BACKGROUND

There has conventionally been known an optical scanning apparatus in which an optical fiber is vibrated at the emitting end part thereof, so as to irradiate light toward an observation object to scan the observation object (see Patent Literature (PTL) 1). The optical scanning apparatus includes a permanent magnet attached to the emitting end part of the optical fiber and a scanning part having four coils each disposed on the respective inner walls of the housing around the permanent magnet. Of the four coils, two coils facing each other constitute X-coils for driving the emitting end part of the optical fiber in the X-axis direction, and the other two coils constitute Y-coils for driving the emitting end part of the optical fiber in the Y-axis direction perpendicular to the X-axis direction.

The X-coils are supplied with a current having a frequency corresponding to the resonance frequency of a vibration portion including the emitting end part of the optical fiber and the permanent magnet. The Y-coils are supplied with a current having a frequency lower than the resonance frequency. With this configuration, the scanning part resonantly vibrates the vibration portion in the X-axis direction through an electromagnetic force while vibrating the vibration portion at a frequency lower than that in the X-axis direction, so as to raster scan the observation object.

CITATION LIST

Patent Literature

PTL 1: JP 2008-116922 A

SUMMARY

Meanwhile, the aforementioned optical scanning apparatus using an optical fiber has an advantageous feature in that the scanning part can be reduced in size. Accordingly, when applied to an endoscope, the insertion tip end may be thinned in diameter as compared with an electronic endoscope which has a solid state image sensor disposed in the insertion tip end part of the endoscope.

On the other hand, the optical scanning apparatus having the scanning part reduced in size means that the vibration amplitude of the optical fiber is small, with the result that the scanning range of the observation object is narrowed. To increase the maximum vibration amplitude of the optical fiber without increasing the scanning part in size, it may be conceivable to increase a drive current to be supplied to driving coils such as X-coils and Y-coils or to increase the size of the permanent magnet, to thereby increase the electromagnetic force for vibrating the optical fiber.

However, such increase in current supplied to the driving coils may result in significant heat generation, which supposedly affects the examinee or causes the driving coils to melt. The permanent magnet, if simply increased in size, may supposedly interfere with the driving coils or the housing when the permanent magnet is displaced along with the optical fiber.

An optical scanning apparatus disclosed herein is for scanning an object by irradiating the object with light emitted from an emitting end face of an optical fiber while vibrating an emitting end part of the optical fiber by a scanning part, the scanning part including: at least a pair of first direction coils which are disposed opposite to each other in the first direction across the emitting end part and vibrate the emitting end part in the first direction; and a permanent magnet installed in the emitting end part as having the emitting end part penetrated therethrough, in which: the permanent magnet is magnetized in the axial direction of a through hole penetrated by the emitting end part; the scanning part drives, by a current supplied to the first direction coils, the emitting end part to vibrate in the first direction near the frequency of the second or higher-order resonance mode such that the vibration has nodes positioned inside the permanent magnet; and the first direction coils are closer in relative distance in the first direction to the permanent magnet than that in other directions when in a state of non-vibration.

DETAILED DESCRIPTION

Hereinafter, Embodiments of the present disclosure will be illustrated with reference to the accompanying drawings.

(Embodiment 1)

Figure 1:
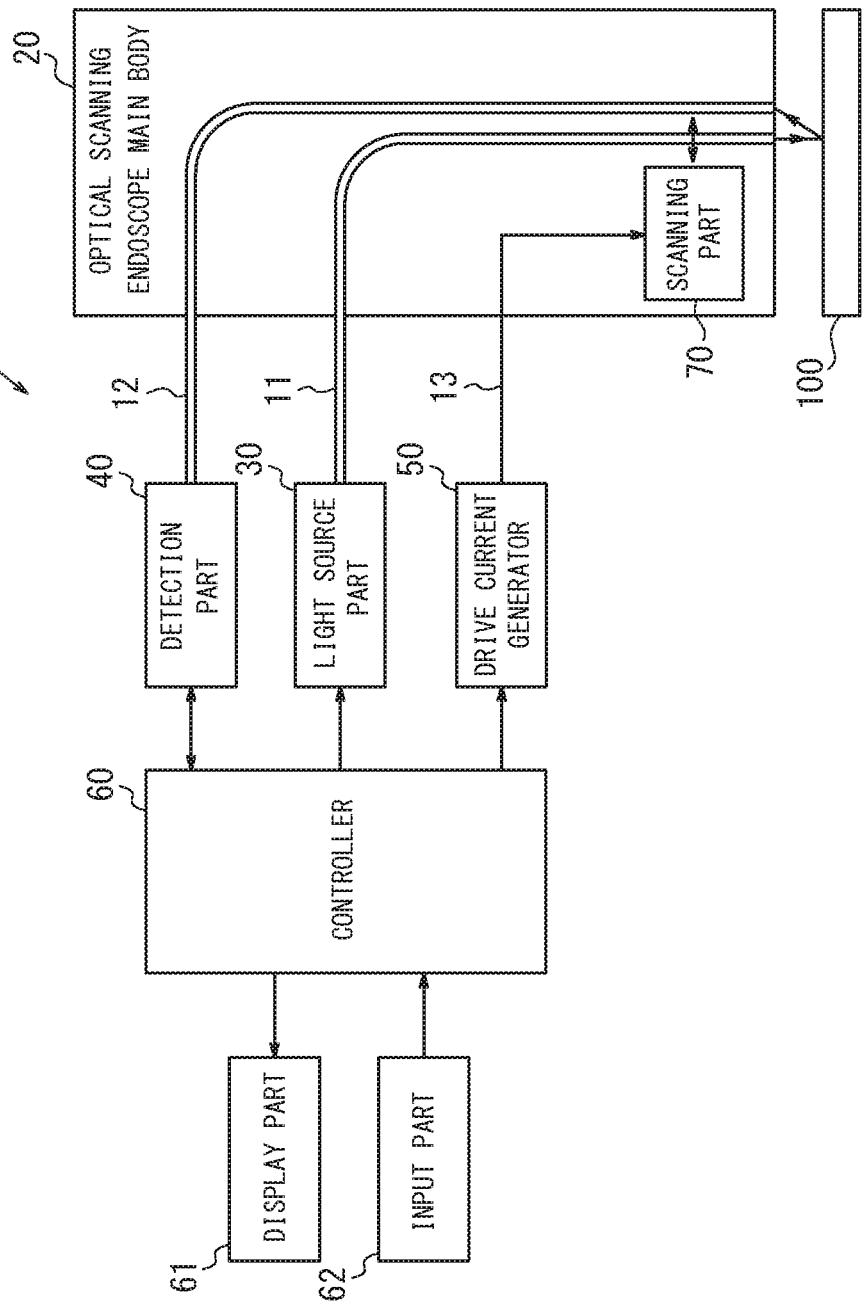
FIG. 1 is a block diagram illustrating a schematic configuration of an optical scanning apparatus according to Embodiment 1 of the present disclosure.

FIG. 1 is a block diagram illustrating a schematic configuration of an optical scanning apparatus according to Embodiment 1. The optical scanning apparatus of FIG. 1 constitutes an optical scanning endoscope apparatus 10, which includes: an optical scanning endoscope main body 20; a light source part 30; a detection part 40; a drive current generator 50; a controller 60; a display part 61; and an input part 62. The light source part 30 and the optical scanning endoscope main body 20 are optically connected to each other via an illumination optical fiber 11 including, for example, one single mode fiber. The detection part 40 and the optical scanning endoscope main body 20 are connected to each other via a detection optical fiber bundle 12 including, for example, a plurality of multimode fibers. The light source part 30, the detection part 40, the drive current generator 50, and the controller 60 may be accommodated in the same housing, or may be in separate housings.

The light source part 30 multiplexes lights from three laser light sources each emitting continuous wave (CW) laser light of, for example, three primary colors of red, green, and blue, respectively, and emits the multiplexed light as white light. The laser light source may use, for example, a diode pumped solid state (DPSS) laser and a laser diode. Naturally, the light source part 30 is not limited to the aforementioned configuration, and may use a single laser source or a plurality of other light sources.

The optical scanning endoscope main body 20 irradiates the observation object (object) 100 with light emitted from the light source part 30 via the optical fiber 11 while vibrating the emitting end part of the optical fiber 11 by a scanning part 70, to thereby two-dimensionally scan (raster scan in Embodiment 1) the observation object 100. Further, the optical scanning endoscope main body 20 converges signal light obtained through the two-dimensional scanning of the observation object 100 to transmit the converged light via the optical fiber bundle 12 to the detection part 40. Here, the drive current generator 50 feeds, via a wiring cable 13, a vibration current required for the scanning part 70, based on the control from the controller 60.

The detection part 40 separates the signal light transmitted through the optical fiber bundle 12 into spectral components, and photoelectrically convert the signal light thus separated into an electric signal. The controller 60 synchronously controls the light source part 30, the detection part 40, and the drive current generator 50, and displays an image on the display part 61 by processing the electric signal output by the detection part 40. Further, the controller 60 makes various settings such as the scanning speed and the brightness of the display image, based on a signal input through input operation of the input part 62.

Figure 2:
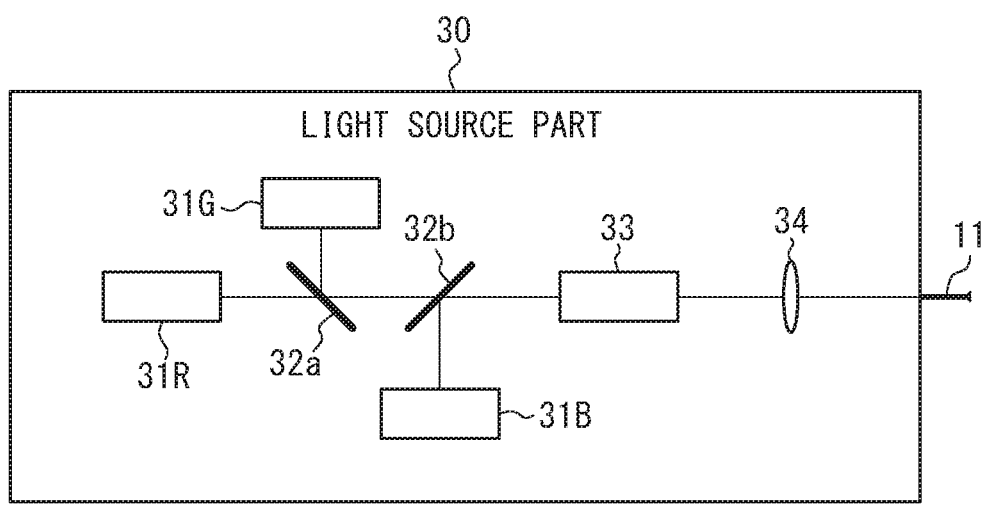
FIG. 2 illustrates a schematic configuration of the light source part of FIG. 1.

FIG. 2 illustrates a schematic configuration of the light source part 30 of the optical scanning endoscope apparatus 10 of FIG. 1. The light source part 30 includes: laser light sources 31R, 31G, 31B emitting a continuous wave (CW) laser light of three primary colors of red, green, and blue; dichroic mirrors 32a, 32b; an acoustic optical modulator (AOM) 33; and a lens 34. The laser slight source 31R of red may use, for example, a semiconductor laser (laser diode (LD)). The laser light source 31G of green may use, for example, a diode pumped solid state laser (DPSS laser). The laser light source 31B of blue may use, for example, a laser diode (LD).

A red laser light emitted from the laser light source 31R sequentially passes through the dichroic mirror 32a and the dichroic mirror 32b in this order. A green laser light emitted from the laser light source 310 is reflected by the dichroic mirror 32a to be coaxially multiplexed with red laser light, to pass through the dichroic mirror 32b. A blue laser light emitted from the laser slight source 31B is reflected by the dichroic mirror 32b to be coaxially multiplexed with the red laser light and the green laser light. In this manner, the dichroic mirror 32b emits white laser light obtained by multiplexing laser lights of three primary colors of red, green, and blue.

The white laser light emitted from the dichroic mirror 32b is intensity-modulated by the AOM 33 to be incident on the incident end of the optical fiber 11 via the lens 34. The AOM 33 modulates the intensity of white laser light to be incident on the optical fiber 11, under the control of the controller 60 of FIG. 1. Here, the laser sources 31R, 31G, 31B and the dichroic mirrors 32a, 32b may not be limitedly arranged as illustrated in FIG. 2, and may be arranged, for example, so as to multiplex green and blue laser lights and then multiplex red laser light. The laser light may be intensity modulated by directly modulating the current of the LD, without using the AOM 33.

Figure 3:
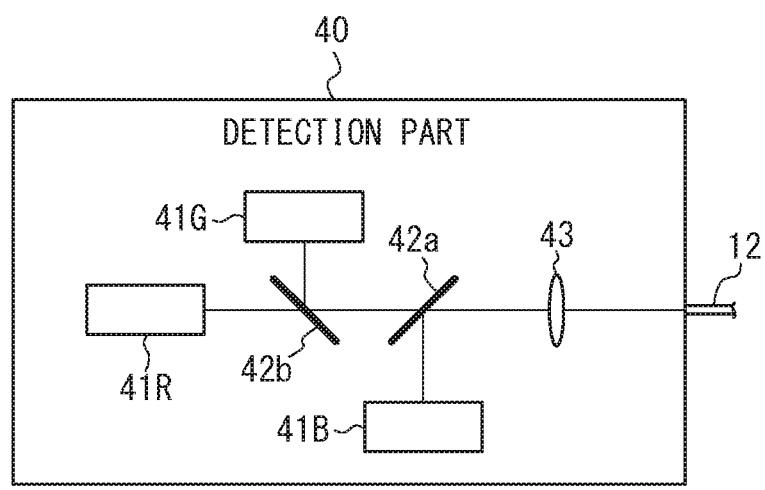
FIG. 3 illustrates a schematic configuration of the detection part of FIG. 1.

FIG. 3 illustrates a schematic configuration of the detection part 40 of the optical scanning endoscope apparatus 10 of FIG. 1. The detection part 40 includes: photodetectors 41R, 41G, 41B using photodiode for detecting light corresponding to each color of red, green, and blue; dichroic mirrors 42a, 42b; and a lens 43. The detection part 40 has the optical fiber bundle 12 connected thereto.

Signal light emitted from the emitting end part of the optical fiber bundle 12 is converted into a substantially parallel light flux by the lens 43, and then have light in a wavelength range of blue reflected and separated by the dichroic mirror 42a while having light in a wavelength of red and green transmitted through the dichroic mirror 42a. The light in the wavelength range of blue separated by the dichroic mirror 42a is received by the photodetector 41B and subjected to photoelectric conversion. Of the light in the wavelength range of red and green having transmitted through the dichroic mirror 42a, the light in the wavelength range of green is reflected by the dichroic mirror 42b while the light in the wavelength range of red is transmitted therethrough to be separated from each other. The green and red signal lights thus separated by the dichroic mirror 42b are each received by the photodetectors 41G and 41R, respectively, to be subjected to photoelectric conversion.

The photoelectrically-converted outputs of the photodetectors 41R, 41G, and 41B are input to the controller 60 of FIG. 1. Here, the photodetetors 41R, 41G, 41B, and the dichroic mirrors 42a, 42b may not be limitedly arranged as illustrated in FIG. 3, and may be arranged, for example, so as to first separate red light from the signal light and then to further separate green and blue signal lights.

Figure 4:
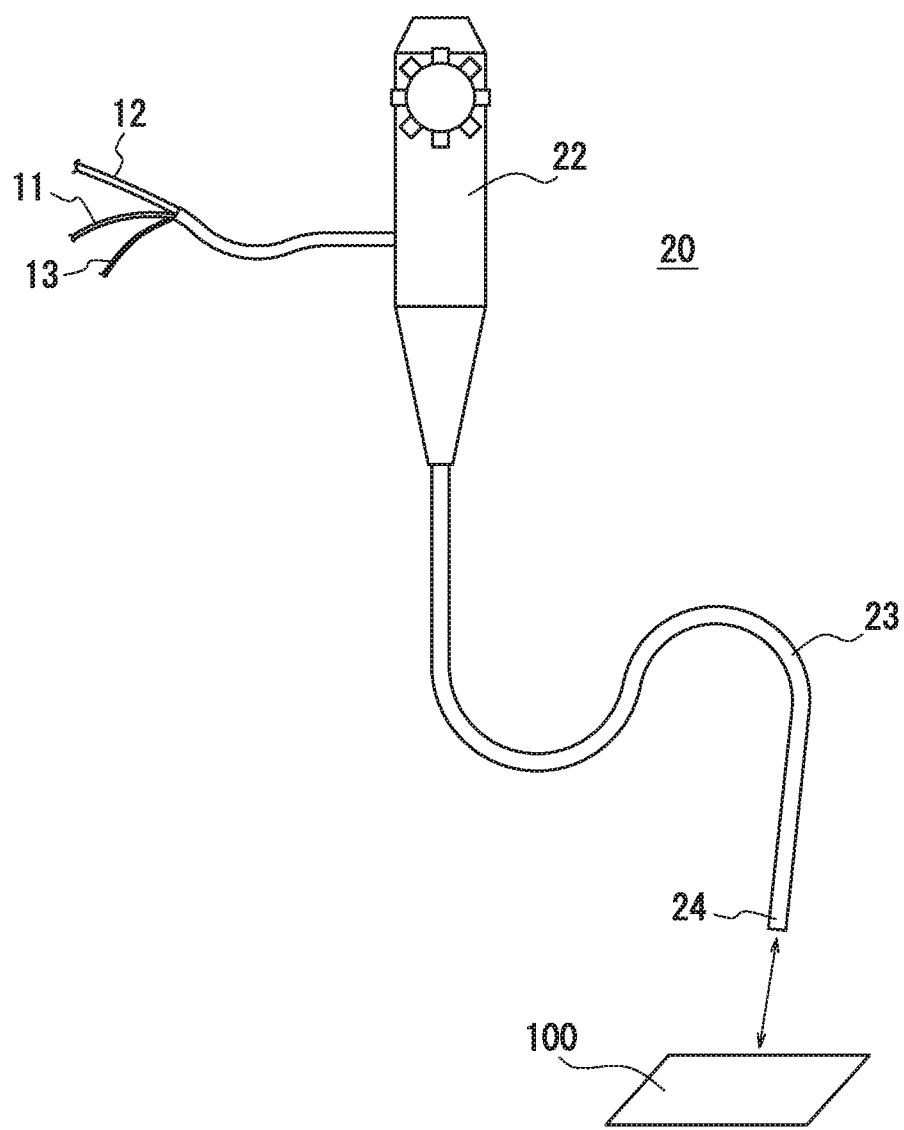
FIG. 4 is an overview schematically illustrating the optical scanning endoscope main body of FIG. 1.

FIG. 4 is an overview schematically illustrating the optical scanning endoscope main body 20. The optical scanning endoscope main body 20 includes an operation portion 22 and a flexible insertion portion 23. The optical fiber 11 connected to the light source part 30, the optical fiber bundle 12 connected to the detection part 40, and the wiring cable 13 from the drive current generator 50 are guided through inside the insertion portion 23 to a tip end part 24. The tip end part 24 is operated by the operation portion 22 to be changed in orientation.

Figure 5:
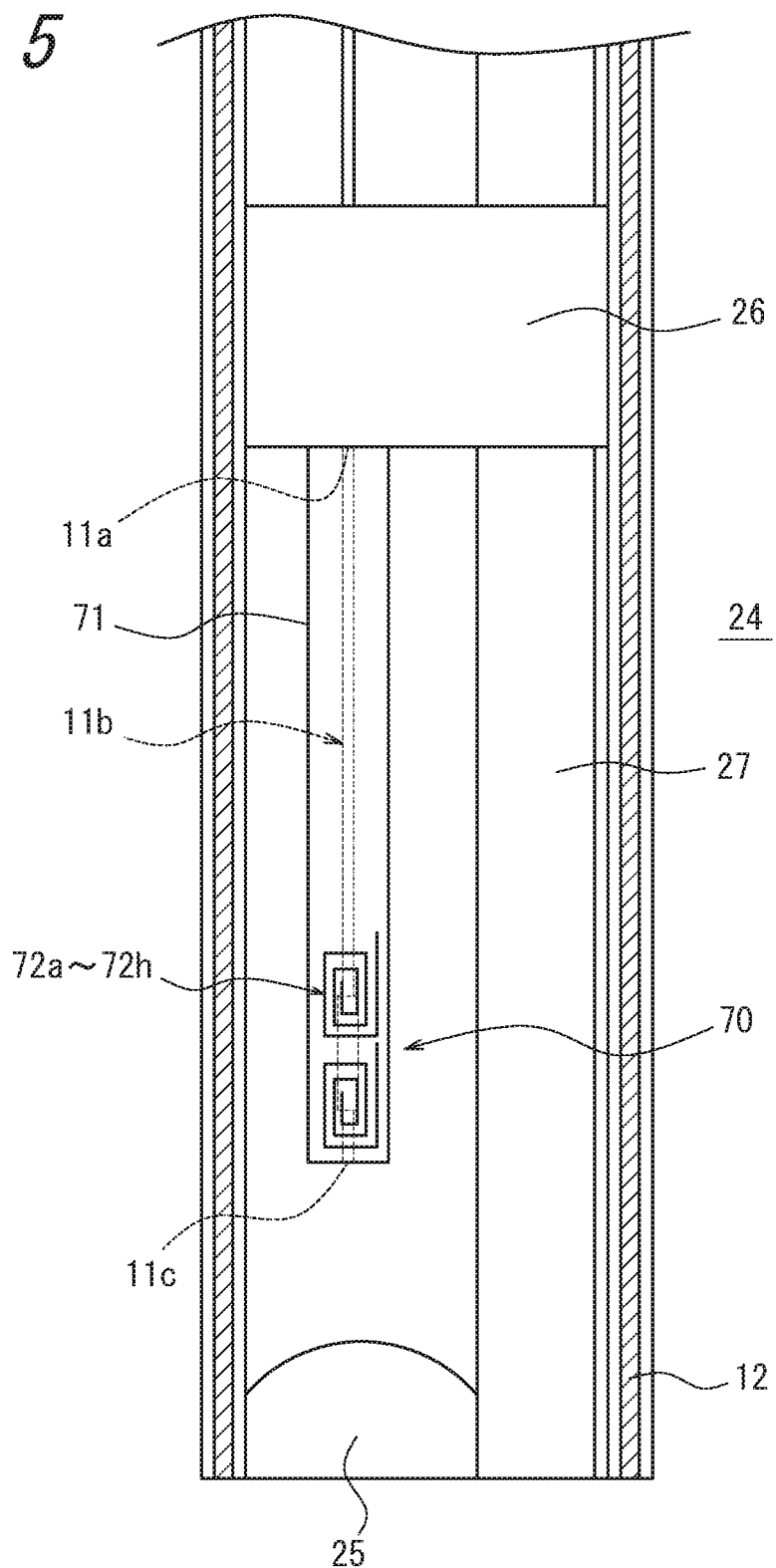
FIG. 5 is an enlarged sectional view of the tip end of the insertion portion of FIG. 4.
Figure 6:
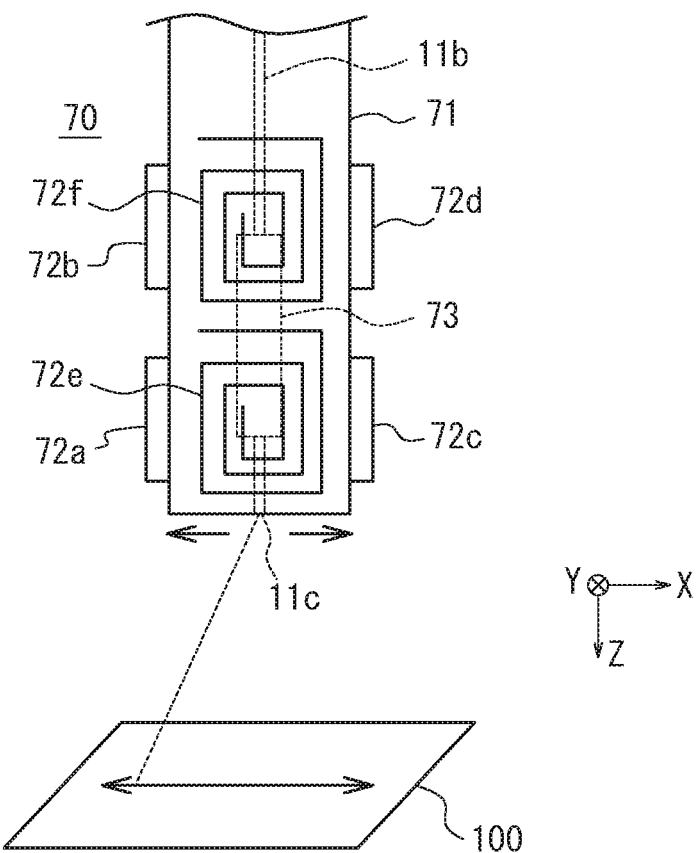
FIG. 6 is an enlarged view of the scanning part of FIG. 5.

FIG. 5 is an enlarged sectional view of the tip end part 24 of the insertion portion 23 of FIG. 4. FIG. 6 is an enlarged view of the scanning part 70 of FIG. 5. The tip end part 24 includes the scanning part 70 and a projection lens 25, while having the optical fiber 11 and the optical fiber bundle 12 that run through the insertion portion 23, and an instrument channel 27 to have various treatment tools inserted therethrough. The optical fiber bundle 12 may have a detection lens at the tip thereof.

In the tip end part 24, the optical fiber 11 is partially fixed, at a fixed part 11*a*, to an attachment ring 26 fixed inside the tip end part 24, while having an emitting end part 11*b* oscillatably supported, the emitting end part 11*b* being defined between the fixed part 11*a* and the emitting end face 11*c* for emitting laser light toward the observation object 100. Meanwhile, the optical fiber bundle 12 is arranged such that each optical fiber passes through the circumferential part of the insertion portion 23, and extends through to the tip of the tip end part 24.

The scanning part 70 is formed of: an angular tube 71 which has electromagnetic coils 72*a* to 72*h* for generating a deflecting magnetic field; and a permanent magnet 73. The electromagnetic coils 72*a* to 72*h* are disposed as spirally wound flat on four side faces of the angular tube 71, and the permanent magnet 73 is installed in part of the emitting end part 11*b* as having the emitting end part 11*b* penetrating therethrough. The angular tube 71 is fixed at one end thereof to the attachment ring 26 so as to enclose, as a tube member, around the emitting end part 11*b*. The permanent magnet 73 is magnetized in the axial direction of the optical fiber 11. The electromagnetic coils 72*a* to 72*h* are provided to the angular tube 71 so as to face one another across each magnetic pole of the permanent magnet 73.

The electromagnetic coils 72*a* to 72*d* constitute two pairs of X-direction coils for vibrating the emitting end part 11*b* in the X-direction (first direction), in which the electromagnetic coils 72*a*, 72*c* form a pair of coils disposed opposite to each other in the X-direction across one magnetic pole of the permanent magnet 73, while the electromagnetic coils 72*b*, 72*d* form a pair of coils disposed opposite to each other in the X-direction across the other magnetic pole of the permanent magnet 73. The electromagnetic coils 72*e* to 72*h* constitute two pairs of Y-direction coils for vibrating the emitting end part 11*b* in the Y-direction (second direction) perpendicular to the X-direction, in which the electromagnetic coils 72*e*, 72*g* form a pair of coils disposed opposite to each other in the Y-direction across one magnetic pole of the permanent magnet 73, while the electromagnetic coils 72*f*, 72*h* form a pair of coils disposed opposite to each other in the Y-direction across the other magnetic pole of the permanent magnet 73. The electromagnetic coils 72*g*, 72*h* are not shown. The electromagnetic coils 74*a* to 74*h* are each disposed such that the winding center axis of each coil intersects, preferably at substantially right angles, with the Z-direction perpendicular to the magnetization direction of the permanent magnet 73, namely, the X-direction and the Y-direction, when the emitting end part 11*b* is in a state of non-vibration.

The electromagnetic coils 72*a* to 72*h* are connected to the drive current generator 50 via the wiring cable 13, and supplied with a necessary current from the drive current generator 50. This way vibrates the emitting end part 11*b* in the X-direction and Y-direction, to thereby raster scan the observation object 100 with laser light.

The projection lens 25 is arranged on the end face side of the tip end part 24. The projection lens 25 substantially converges, onto the observation object 100, laser light emitted from the emitting end face 11*c* of the optical fiber 11. Further, the detection lens may be arranged to take in, as detection light, the laser light converged onto the observation object 100 and reflected, scattered, and refracted by the observation object 100 (light that has interacted with the observation object 100) or fluorescence, and to converge the light thus taken in, onto the optical fiber bundle 12 disposed behind the detection lens.

Figure 7:
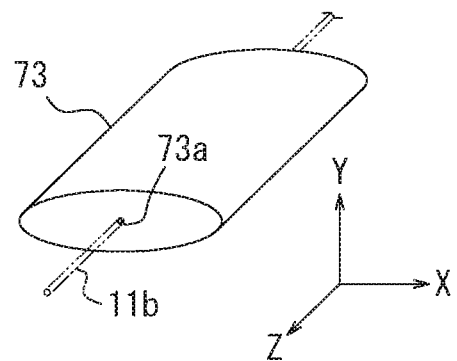
FIG. 7 is an enlarged perspective view of the permanent magnet of FIG. 6.

In Embodiment 1, the permanent magnet 73 is in an asymmetric elliptic cylinder shape, as illustrated in the enlarged perspective view of FIG. 7, when viewed in the axial direction of a through hole 73*a* of the emitting end part 11*b*, the axial direction being aligned parallel with the Z-direction. In FIG. 7, the permanent magnet 73 is longer in the X-direction than in the Y-direction. Accordingly, the emitting end part 11*b*, when in a state of non-vibration, has a relative distance from the permanent magnet 73 to each of the electromagnetic coils 72*a*, 72*c*; 72*b*, 72*d* forming pairs in the X-direction that is smaller than the relative distance to each of the electromagnetic coils 72*e*, 72*g*; 72*f*, 72*h* forming pairs in the other direction, namely, in the Y-direction.

Figure 8:
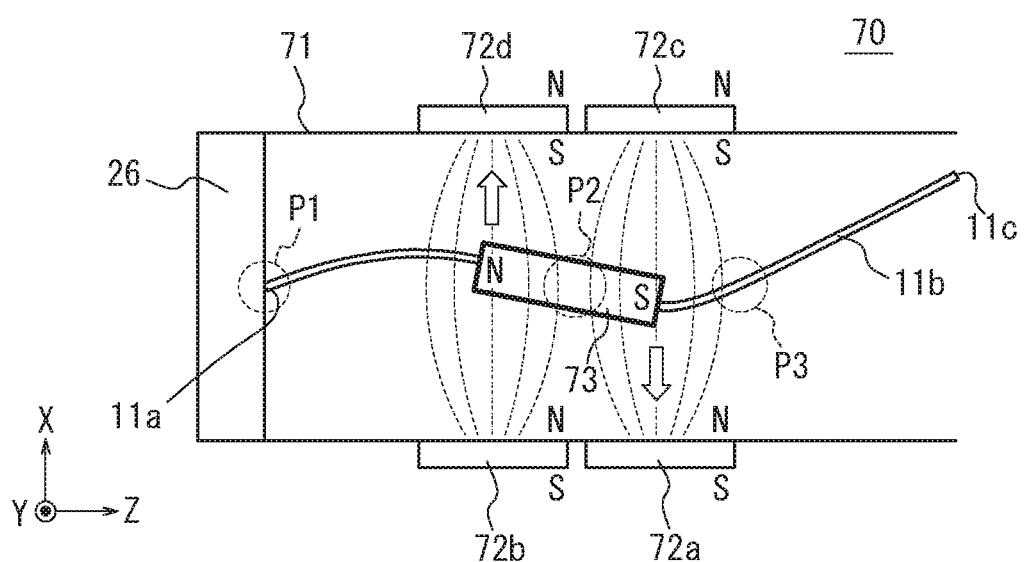
FIG. 8 is for illustrating a vibration state of the vibration part in the X-direction in the third-order resonance mode.

Then, as illustrated in FIG. 8, the electromagnetic coils 72*a*, 72*c*; 72*b*, 72*d* forming pairs in the X-direction are supplied with power such that, for example, forces oriented mutually opposite in the +X-direction and the −X-direction (indicated by the arrows of FIG. 8) are to act, at a given moment, on the permanent magnet 73 at both ends in the magnetization direction. This configuration allows the emitting end part 11*b* to be driven to vibrate, in the X-direction, in proximity to the resonance frequency of the third-order resonance mode having nodes of vibration each in the vicinity of a region P1 of a fixed portion to the fixed part 11*a*, in the vicinity of a region P2 inside the permanent magnet 73, and in the vicinity of a region P3 near the permanent magnet 73 between the permanent magnet 73 and the emitting end face 11*c*, respectively. Further, the electromagnetic coils 72*e*, 72*g*; 72*f*, 72*h* forming pairs in the Y-direction are supplied with power such that, for example, forces oriented the same in the +Y-direction are to act, at a given moment, on the permanent magnet 73 at both ends in the magnetization direction that is larger in relative distance to the coils 72*e*, 72*g*; 72*f*, 72*h*. This configuration allows the emitting end part 11*b* to be driven to vibrate, in the Y-direction, in proximity to the resonance frequency of the first-order resonance mode having a node of vibration in the vicinity of the region P1. In FIG. 8, the electromagnetic coils 72*a*, 72*c*; 72*b*, 72*d* generate magnetic fields indicated by the broken lines.

As described above, in the vibration in the X-direction, the vibration node may be positioned inside the permanent magnet 73 so as to reduce the displacement of the permanent magnet 73 during vibration. Accordingly, the electromagnetic coils 72*a*, 72*c*; 72*b*, 72*d* may be arranged in proximity to the permanent magnet 73, to thereby cause the magnetic fields generated by the electromagnetic coils 72*a*, 72*c*; 72*b*, 72*d* to effectively act on the permanent magnet 73. This way allows the emitting end part 11*b* to efficiently vibrate in proximity to the resonance frequency of the third-order resonance mode. Further, the permanent magnet 73 is larger in the X-direction length passing through the through hole 73*a* than in the Y-direction length passing through the through hole 73*a*, in section perpendicular to the axial direction of the through hole 73*a*, and thus, the permanent magnet 73 can be disposed closer, in the X-direction, to the electromagnetic coils 72*a*, 72*c*; 72*b*, 72*d*. This way allows the magnetic fields generated by the electromagnetic coils 72*a*, 72*c*; 72*b*, 72*d* to effectively act on the permanent magnet 73.

Meanwhile, in a case where the resonance frequency in the X-direction and the resonance frequency in the Y-direction are close to each other, when the emitting end part 11b is driven to vibrate near the resonance frequency only in the X-direction, an undesired vibration may also be generated in the Y-direction, which may render an unintended elliptical locus. However, the aforementioned configuration is capable of obtaining a desired vibration locus such as straight locus, without generating such elliptical locus. Further, the coils are disposed in proximity to the end face of the permanent magnet 73 such that the winding center axis of each coil intersects with the Z-direction as the magnetization direction of the permanent magnet 73 when the emitting end part 11b is in a state of non-vibration. Accordingly, the coils generate magnetic fields that intersect with the magnetization direction of the permanent magnet 73, and the magnetic fields thus intersecting with the magnetization direction effectively act on the magnetic poles on the end face of the permanent magnet 73. In this manner, the magnetic force to act on the permanent magnet 73 is applied in the same direction as that of the vibration of the permanent magnet 73 necessary to excite the vibration of the emitting end part 11b, which can efficiently vibrate the emitting end part 11b. Further, the angular tube 71 for accommodating the emitting end part 11b is provided, so as to readily hold the electromagnetic coils 72a to 72h on four side faces of the angular tube 71. The angular tube 71 may be, for example, round in shape.

Figure 9:
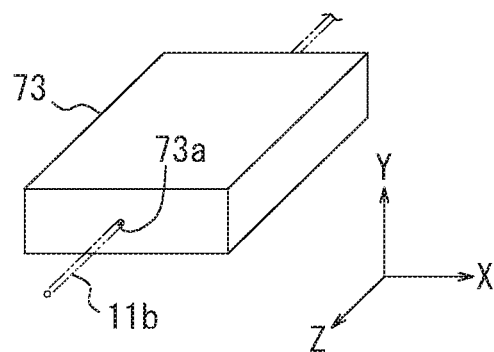
FIG. 9 is an enlarged perspective view of a modification of the permanent magnet.

Here, the third-order resonance mode in the X-direction may be in a range of ±several %, preferably of ±1%, based on the resonance frequency fx in the X-direction of the vibration part including the emitting end part 11b and the permanent magnet 73. Similarly, the first-order resonance mode in the Y-direction may be in a range of ±several %, preferably of ±1%, based on the resonance frequency fy in the Y-direction of the vibration part. In this manner, Embodiment 1 can efficiently vibrate, without increasing the size of the scanning part 70, the emitting end face 11c of the optical fiber 11 at high speed with a large amplitude in the X-direction and at low speed with a large amplitude in the Y-direction, to thereby raster scan the observation object 100 over a wide range. Thus, the optical scanning endoscope apparatus 10 can efficiently increase the maximum vibration amplitude of the illumination optical fiber 11 without increasing the scanning part 70 in size. The permanent magnet 73 may be formed as an asymmetric rectangular prism with a rectangle longer in the X-direction than in the Y-direction when viewed in the Z-direction, as illustrated in the enlarged perspective view of FIG. 9.

In this embodiment, the electromagnetic coils 72a, 72c; 72b, 72d; 72e, 72f; 72g, 72h are disposed opposite to each other at least on a magnetic pole side opposite to the emitting end face side of the permanent magnet 73. The electromagnetic coils 72e, 72f; 72g, 72h are disposed closer to the permanent magnet 73 than are the electromagnetic coils 72a, 72c; 72b, 72d, with the emitting end part being in a state of non-vibration. This configuration allows the permanent magnet 73 to be disposed closer, in the X-direction, toward the electromagnetic coils 72a, 72c; 72b, 72d and further allows the electromagnetic coils 72e, 72f; 72g, 72h to be disposed closer, in the Y-direction, to the permanent magnet, to thereby effectively apply the magnetic fields generated by the electromagnetic coils 72a, 72c; 72b, 72d and electromagnetic coils 72e, 72f; 72g, 72h to the permanent magnet 73 while allowing the permanent magnet 73 to remain asymmetric in shape.

Further, the pair of coils is each disposed to have a winding center axis of the coil positioned in the vicinity of the end face relative to the magnetization direction of the permanent magnet 73. Thus, the coils generate a magnetic field in a direction intersecting with the magnetization direction of the permanent magnet 73, and the magnetic field in a direction intersecting with the magnetization direction acts on a magnetic pole on the end face of the permanent magnet 73. The direction of the magnetic force coincides with the vibration direction of the permanent magnet 73 necessary for exciting the vibration of the optical fiber 11, and thus, the optical fiber 11 can be efficiently vibrated.

Moreover, the pair of coils is each disposed to have a winding center axis of the coil intersecting, substantially at right angles, with the polarization direction of the permanent magnet. This configuration allows the pair of coils to generate a magnetic field that may further efficiently act on the permanent magnet 73.

(Embodiment 2)

Figure 10:
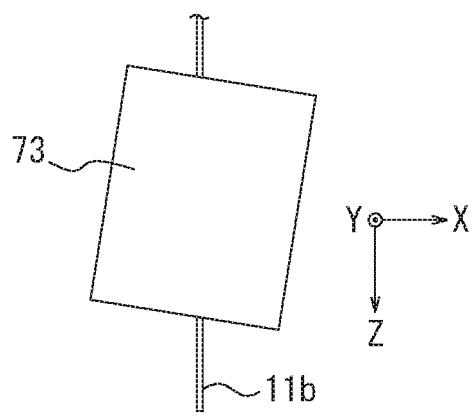
FIG. 10 illustrates the permanent magnet for illustrating Embodiment 2.

In the optical scanning apparatus according to Embodiment 2, the permanent magnet 73 constituting the scanning part 70 in the optical scanning apparatus of Embodiment 1 is mounted onto the emitting end part 11b as being inclined in the X-direction as illustrated in FIG. 10. With this configuration, the resonance frequencies in the X-direction and in the Y-direction of the vibration part may have a larger difference as compared with the case where the permanent magnet 73 is imparted asymmetry only in the shape thereof, and thus, in addition to the effect of Embodiment 1, the vibration part may be driven to vibrate with more ease in the third-order resonance mode in the X-direction and in the first-order resonance mode in the Y-direction.

The permanent magnet 73 may be mounted, as a cylinder or a rectangular prism that is square in section perpendicular to the longitudinal direction, onto the emitting end part 11b as being inclined in the X-direction, so as to be asymmetric when viewed in the Z-direction.

(Embodiment 3)

Figure 11:
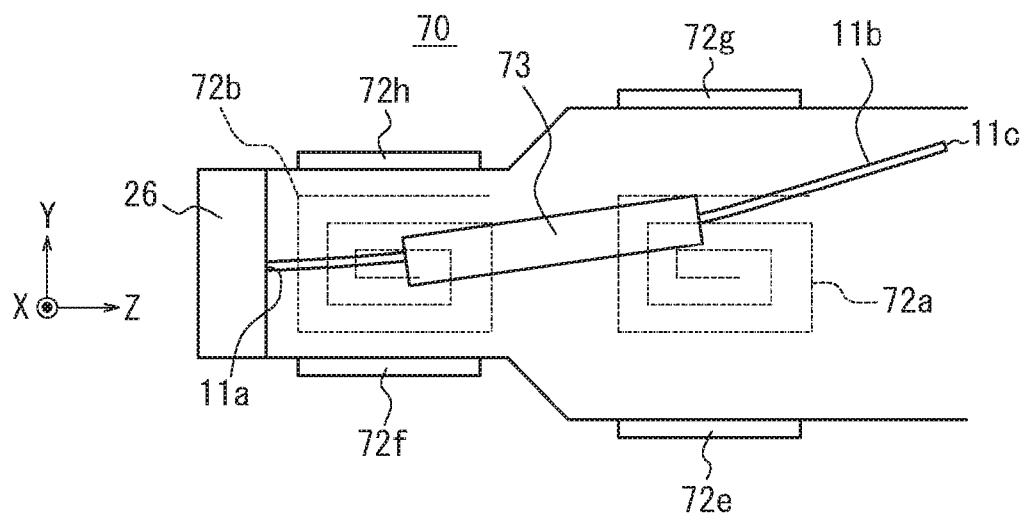
FIG. 11 illustrates a configuration of the scanning part for illustrating Embodiment 3.

The optical scanning apparatus according to Embodiment 3 is different in configuration of the scanning part 70, from the optical scanning apparatus according to Embodiment 1 or Embodiment 2. Specifically, in the scanning part 70, as illustrated in FIG. 11, the electromagnetic coils 72f, 72h disposed opposite to each other in the Y-direction on the magnetic pole opposite to the emitting end face 11c side of the permanent magnet 73, are arranged closer to the permanent magnet 73 than are the electromagnetic coils 72e, 72g disposed opposite to each other in the Y-direction, when the emitting end part 11b is in a state of non-vibration. In other words, the angular tube 71 is smaller in opening where the electromagnetic coils 72f, 72h are arranged than in opening where the electromagnetic coils 72e, 72g are arranged. In addition to the effect produced in Embodiment 1, this configuration is capable of enhancing the electromagnetic effect between the electromagnetic coils 72f, 72h and the permanent magnet 73 as the distance therebetween is closer.

Accordingly, the vibration amplitude in the Y-direction in the first-order resonance mode can be increased, when the current supplied to the electromagnetic coils 72f, 72h is the same as those in Embodiments 1 and 2. When the vibration amplitude in the Y-direction in the first-order resonance mode remains the same as those in Embodiments 1 and 2, the current to be supplied to the electromagnetic coils 72f, 72h may be reduced. Further, this constitution allows the coils to be held with a simple configuration, and to be disposed at a position further closer to the permanent magnet.

(Embodiment 4)

Figure 12:
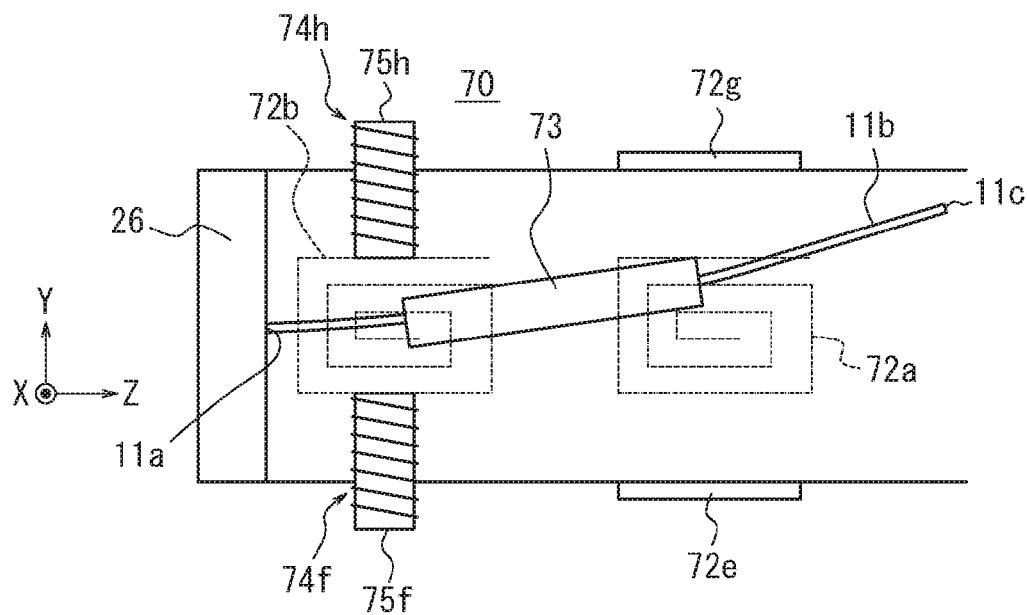
FIG. 12 illustrates a configuration of the scanning part for illustrating Embodiment 4.

Similarly to the case of Embodiment 3, the optical scanning apparatus of Embodiment 4 is different in configuration of the scanning part 70, from the optical scanning apparatus of Embodiment 1 or 2. Specifically, in the scanning part 70, as illustrated in FIG. 12, the electromagnetic coils 72f, 72h disposed opposite to each other in the Y-direction on the magnetic pole opposite to the emitting end face 11c side of the permanent magnet 73, are replaced by solenoid electromagnetic coils 74f, 74h disposed on the angular tube 71. The solenoid electromagnetic coils 74f, 74h are each formed of a coil wound around the outer circumference of a core rod 75f, 75h, respectively. The core rods 75f, 75h are each formed of a paramagnetic material such as stainless steel, or of a ferromagnetic material such as iron and permalloy, and disposed closer to the permanent magnet 73 than are the electromagnetic coils 72b, 72d disposed opposite to each other in the X-direction, with the emitting end part 11b being in a state of non-vibration.

Therefore, according to Embodiment 4, as in the case of Embodiment 3, the electromagnetic effect between the solenoid electromagnetic coils 74f, 74h and the permanent magnet 73 can be enhanced as the distance therebetween is closer, to thereby allow the emitting end part 11b to be efficiently vibrated in the first-order vibration mode in the Y-direction. Further, the core rods 75f, 75h as being formed of a ferromagnetic material can further enhance the electromagnetic effect, to thereby generate a grater magnetic field while reducing a current to be supplied to the solenoid electromagnetic coils 74f, 74h. Here, the solenoid electromagnetic coils 74f, 74h may be air core coils.

(Embodiment 5)

Figure 13A:
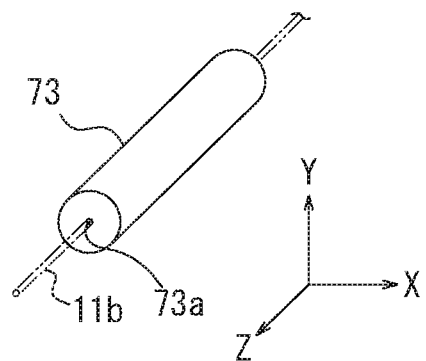
FIG. 13A illustrates one example of the permanent magnet for illustrating Embodiment 5.
Figure 13B:
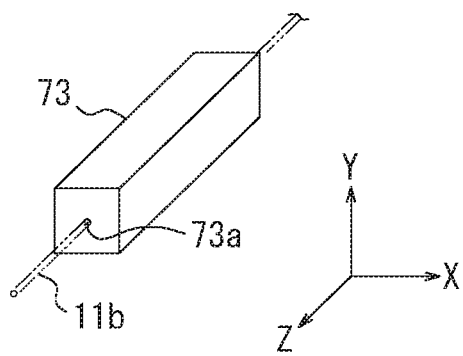
FIG. 13B illustrates another example of the permanent magnet for illustrating Embodiment 5.

In Embodiments described above, as illustrated in FIGS. 7, 9, and 10, the permanent magnet 73 is formed in an asymmetric shape when viewed from the axial direction of the through hole 73a so as to reduce the relative distance between the permanent magnet 73 and the coils in the first direction (first direction coils) as compared with the relative distance between the permanent magnet 73 and the coils in the second direction (second direction coils). Embodiment 5 is similar to Embodiment 1, except in that the permanent magnet 73 is formed in a symmetric cylinder or quadrangular prism shape that is equal in distance in the X-direction and Y-direction, when viewed from the axial direction of the through hole 73a, as illustrated in, for example, FIG. 13A or 13B. Here, the permanent magnet 73 is not limited to the configurations of FIGS. 13A and 13B, and may be in an arbitrary shape as long as being equal in length in the X-direction and Y-direction when viewed from the axial direction of the through hole 73a.

Figure 14:
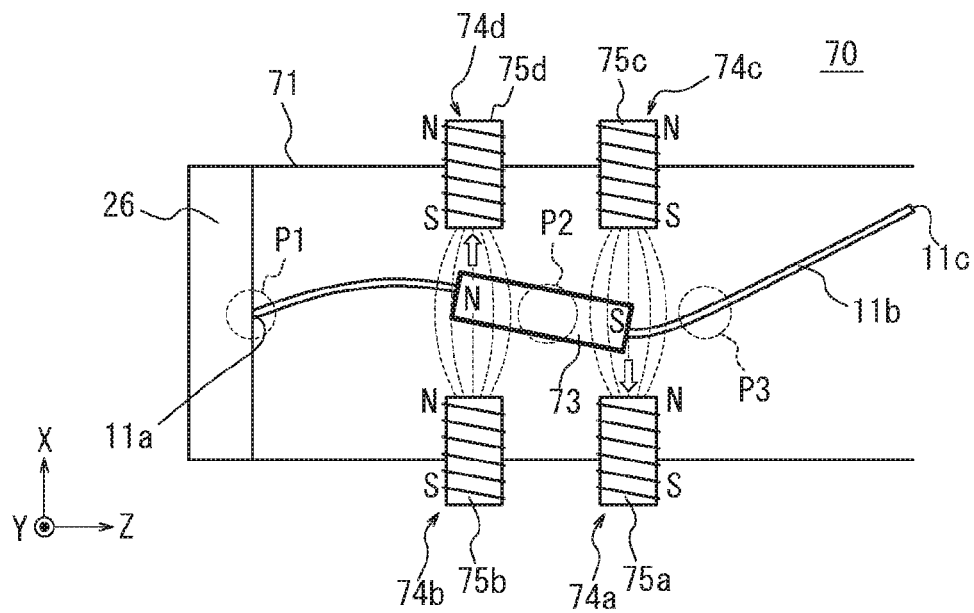
FIG. 14 illustrates a configuration of the scanning part for illustrating Embodiment 5.

Further, the angular tube 71 has two pairs of solenoid electromagnetic coils 74a, 74c and 74b, 74d disposed thereon as illustrated in FIG. 14, in place of the two pairs of the electromagnetic coils 72a, 72c and 72b, 72d disposed opposite to each other in the X-direction. The solenoid electromagnetic coils 74a to 74d are formed of coils each wound around the outer circumference of the core rods 75a to 74d, respectively, similarly to the solenoid electromagnetic coils 74f, 74h of FIG. 12. The core rods 75a to 75d are each formed of a paramagnetic material such as stainless steel or of a ferromagnetic material such as iron and permalloy, and disposed closer to the permanent magnet 73 than are the electromagnetic coils 72e to 72h disposed opposite to each other in the Y-direction, with the emitting end part 11b being in a state of non-vibration. Here, the solenoid electromagnetic coils 74a to 74d may be air core coils.

Figure 15:
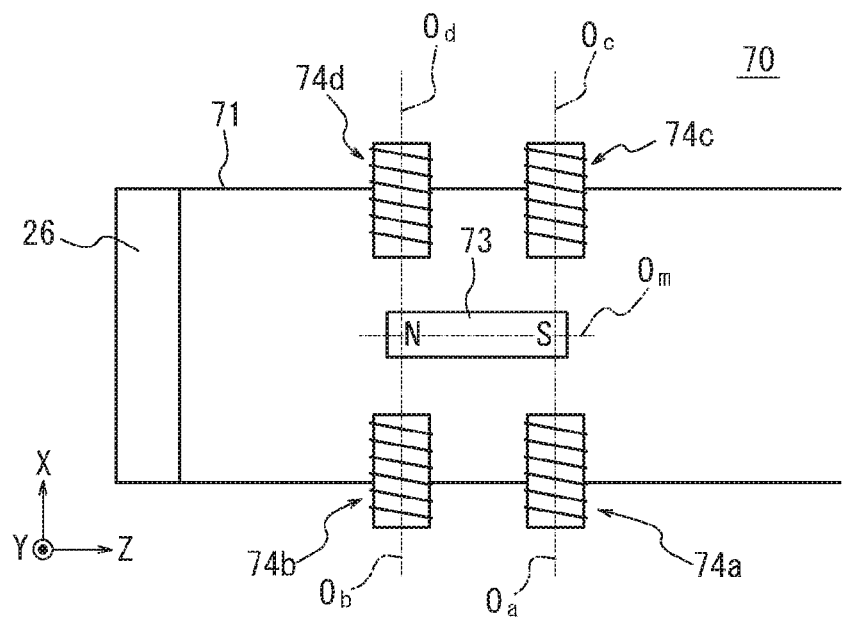
FIG. 15 is for illustrating a relation between the winding center axis of the solenoid electromagnetic coil and the magnetization direction of the permanent magnet of FIG. 14.

Here, the solenoid electromagnetic coils 74a to 74d are each similarly disposed as in Embodiments described above such that, as illustrated in FIG. 15, the winding center axes Oa to Od of the coils are each intersect, preferably at substantially right angles, with the magnetization direction Om of the permanent magnet 73, i.e., in the Z-direction, with the emitting end part 11b being in a state of non-vibration. Although not shown, the electromagnetic coils 72e to 72h disposed opposite in the Y-direction are similarly arranged.

As illustrated in FIG. 14, the solenoid electromagnetic coils 74a, 74c; 74b, 74d forming pairs in the X-direction are supplied with power such that, for example, forces oriented mutually opposite in the +X-direction and the −X-direction (indicated by the arrows of FIG. 14) are to act, at a given moment, on the permanent magnet 73 at both ends in the magnetization direction. Further, the electromagnetic coils 72e, 72g; 72f, 72h forming pairs in the Y-direction are supplied with power such that, for example, forces oriented the same in the +Y-direction are to act, at a given moment, on the permanent magnet 73 at both ends in the magnetization direction. Here, similarly to Embodiments described above, with the emitting end part 11b being in a state of non-vibration, the relative distances from the permanent magnet 73 to the solenoid electromagnetic coils 74a, 74c; 74b, 74d forming pairs in the X-direction is smaller than the relative distances from the permanent magnet 73 to the electromagnetic coils 72e, 72g; 72f, 72h forming pairs in the other direction, i.e., the Y-direction. Here, the broken lines of FIG. 14 show the electric fields generated by the solenoid electromagnetic coils 74a, 74c; 74b, 74d.

Therefore, as in FIG. 8, the emitting end part 11b is efficiently driven to vibrate near the resonance frequency of the third-order resonance mode having, in the X-direction, nodes of vibration each in the vicinity of the region P1 at the fixed portion to the fixing part 11b, in the vicinity of the region P2 inside the permanent magnet 73, and in the vicinity of the region P3 close to the permanent magnet 73 between the permanent magnet 73 and the emitting end face 11c, respectively. Further, the emitting end part 11b is efficiently driven to vibrate, in the Y-direction, near the resonance frequency of the first-order resonance mode having a node of vibration in the vicinity of the region P1. Further, the solenoid electromagnetic coils 74a to 74d may have the core rods 75a to 75d formed of ferromagnetic materials, so as to generate larger magnetic fields with a reduced currents supplied to each of the solenoid electromagnetic coils 74a to 74d, to thereby more efficiently allow the emitting end part 11b to vibrate in the X-direction.

The disclosed optical scanning apparatus is not limited to Embodiments described above, and may be subjected to various modifications and alterations. For example, the configuration of Embodiment 5 having the solenoid electromagnetic coils 74a to 74d may be combined with the configuration of Embodiment 3 having the electromagnetic coils 72f, 72h disposed closer to the permanent magnet 73, or with the configuration of Embodiment 4 including, in place of the electromagnetic coils 72f, 72h, the solenoid electromagnetic coils 74f, 74h. Further, the resonance mode in the X-direction of the emitting end part 11b of the optical fiber 11 is not limited to the third-order resonance mode, and may be the second-order resonance mode or the fourth or higher-order resonance mode as long as the vibration has nodes positioned inside the permanent magnet 73. The resonance mode in the Y-direction is not limited in the vicinity of the resonance frequency of the first-order resonance mode, as long as the drive frequency is lower than the drive frequency in the X-direction. The scanning part 70, which raster scans the observation object 100 by vibrating the emitting end part 11b in the X-direction and Y-direction perpendicular to each other, may also be adapted to perform another scan such as Lissajous scan, or only the first-order scan in the high-order resonance mode having a node of vibration inside the permanent magnet 73. The disclosed apparatus is applicable not only to an optical scanning endoscope apparatus but also to various optical scanning apparatuses.

REFERENCE SIGNS LIST 10 optical scanning endoscope apparatus
11 optical fiber
11a fixed part
11b emitting end part
11c emitting end face
12 optical fiber bundle
20 optical scanning endoscope main body
30 light source part
40 detection part
50 drive current generator
60 controller
70 scanning part
71 angular tube
72a to 72h electromagnetic coil
73 permanent magnet
73a through hole
74a to 74d, 74f, 74h solenoid electromagnetic coil
75a to 75d, 75f, 75h core rod
100 observation object

The invention claimed is:

1. A scanning part for use with an optical scanning apparatus for scanning an object by irradiating the object with light emitted from an emitting end face of an optical fiber while vibrating an emitting end part of the optical fiber, the emitting end part being vibrated by the scanning part, the scanning part comprising:
at least a pair of first direction coils disposed opposite to each other in a first direction across the emitting end part, the pair of first direction coils vibrating the emitting end part in the first direction;
a permanent magnet having a though-hole for accepting the emitting end part penetrated therethrough, and
a controller configured to drive, by a current supplied to the pair of first direction coils, the emitting end part to vibrate in the first direction near a first frequency of second or higher-order resonance mode such that the vibration has nodes positioned inside the permanent magnet;
wherein the permanent magnet is magnetized in an axial direction of the through hole; and
when in a state of non-vibration, each of the pair of first direction coils is closer in relative distance in the first direction to the permanent magnet than each of the first direction coils is in other directions to the permanent magnet.

2. The optical scanning apparatus according to claim 1, wherein the permanent magnet is asymmetric when viewed from the axial direction of the through hole.

3. The optical scanning apparatus according to claim 2, wherein the permanent magnet is, in section perpendicular to the axial direction of the through hole, longer in the first direction passing through the through hole, than in a direction perpendicular to the first direction and passing through the through hole.

4. The optical scanning apparatus according to claim 2, wherein the permanent magnet is disposed so as to be inclined in the axial direction of the through hole.

5. The optical scanning apparatus according to claim 1, further comprising at least a pair of second direction coils disposed opposite to each other in a direction intersecting with the first direction across the emitting end part, the pair of second direction coils vibrating the emitting end part in a second direction intersecting with the first direction, wherein:
the controller is further configured to drive, by a current supplied to the pair of second direction coils, the emitting end part to vibrate in the second direction at a second frequency lower than the first frequency.

6. The optical scanning apparatus according to claim 5, wherein:
the pair of first direction coils and the pair of second direction coils are disposed opposite to each other at least on a magnetic pole side opposite to an emitting end face side of the permanent magnet; and
each of the pair of second direction coils are disposed closer to the permanent magnet than are the pair of first direction coils, with the emitting end part being in a state of non-vibration.

7. The optical scanning apparatus according to claim 5, wherein:
the second direction is perpendicular to the first direction; and
the scanning part raster scans the object with light irradiated from the optical fiber.

8. The optical scanning apparatus according to claim 1, wherein the pair of first direction coils are each disposed to have a winding center axis intersecting with a polarization direction of the permanent magnet in a vicinity of at least one end face of the permanent magnet in a magnetization direction of the permanent magnet.

9. The optical scanning apparatus according to claim 8, wherein the pair of first direction coils are each disposed to have the winding center axis intersecting, substantially at right angles, with the magnetization direction of the permanent magnet.

10. The optical scanning apparatus according to claim 8, further comprising a tube member for accommodating the emitting end part, wherein:
the pair of first direction coils are disposed opposite to each other on side faces of the tube member; and
the tube member has a smaller opening in a portion where the pair of first direction coils are disposed, as compared with other portions of the tube member.

11. The optical scanning apparatus according to claim 1, wherein the pair of first direction coils each have a core rod formed of a ferromagnetic material inserted along the winding center axis.

12. The optical scanning apparatus according to claim 1, wherein the scanning part is installed in an insertion tip end part of an endoscope.

* * * * *